US012766208B2

(12) United States Patent
Nalawade et al.

(10) Patent No.: US 12,766,208 B2
(45) Date of Patent: Oct. 20, 2026

(54) UNIVERSAL DISINFECTING CAP FOR DIFFERENT TYPES OF FEMALE CONNECTORS

(71) Applicant: Becton, Dickinson and Company, Franklin Lakes, NJ (US)

(72) Inventors: Praveen Nalawade, Belagavi (IN); Manish Kumar, Bengaluru (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1023 days.

(21) Appl. No.: 17/979,203

(22) Filed: Nov. 2, 2022

(65) Prior Publication Data

US 2024/0139355 A1 May 2, 2024

(51) Int. Cl.
*A61L 2/16* (2006.01)
*A61L 103/05* (2026.01)
*A61M 39/20* (2006.01)

(52) U.S. Cl.
CPC ............... *A61L 2/16* (2013.01); *A61M 39/20* (2013.01); *A61L 2103/05* (2026.01); *A61L 2202/121* (2013.01); *A61L 2202/15* (2013.01)

(58) Field of Classification Search
CPC ............. A61L 2/0082; A61L 2202/121; A61L 2202/15; A61L 2202/21; A61M 39/20; A61M 39/162
See application file for complete search history.

(56) References Cited

U.S. PATENT DOCUMENTS 8,197,749 B2 6/2012 Howlett et al.
8,523,831 B2 9/2013 Solomon et al.
8,671,496 B2 3/2014 Vaillancourt et al.
8,696,820 B2 4/2014 Vaillancourt et al.
8,740,864 B2 6/2014 Hoang et al.
9,039,989 B2 5/2015 Liu et al.
9,283,369 B2 3/2016 Ma et al.
9,399,125 B2 7/2016 Burkholz
9,480,833 B2 11/2016 Hoang et al.
D834,187 S 11/2018 Ryan
10,376,686 B2 8/2019 Burkholz et al.
10,413,716 B2 9/2019 Sathe
10,871,246 B2 * 12/2020 Marici ................ A61M 39/165
11,083,883 B2 8/2021 Ryan et al.
11,273,298 B2 3/2022 Erekovcanski et al.
11,344,715 B2 5/2022 Erekovcanski et al.
11,389,636 B2 7/2022 Coyle
2012/0302968 A1 11/2012 Tennican
2012/0302997 A1 11/2012 Gardner et al.
2013/0035667 A1 2/2013 Anderson et al.
(Continued)

*Primary Examiner* — Brendan A Hensel
(74) *Attorney, Agent, or Firm* — Servilla Whitney LLC

(57) ABSTRACT

A cap configured to engage different types of female connectors includes a housing having a closed bottom, an open top, and a sidewall extending between the top and the bottom with threads on an inner surface of the sidewall. The cap also includes a sleeve disposed in the housing with threads engaged to the threads of the housing configured to rotate relative to the housing, thereby moving the sleeve through the housing, and a gripper disposed at least partially in the sleeve having at least one flexible leg pressed radially inward by the sleeve as the sleeve moves through the housing. The cap also includes an absorbent support disposed in the gripper configured to clean and/or disinfect portions of the female connector.

19 Claims, 16 Drawing Sheets

(56) References Cited

U.S. PATENT DOCUMENTS

| | | | | |
|---|---|---|---|---|
| 2013/0178804 | A1 | 7/2013 | Tennican | |
| 2013/0197485 | A1 | 8/2013 | Gardner et al. | |
| 2014/0135739 | A1 | 5/2014 | Solomon et al. | |
| 2015/0005699 | A1 | 1/2015 | Burbank et al. | |
| 2015/0086441 | A1 | 3/2015 | She et al. | |
| 2016/0106968 | A1 | 4/2016 | Solomon et al. | |
| 2016/0144118 | A1 | 5/2016 | Solomon et al. | |
| 2016/0310720 | A1 | 10/2016 | Solomon et al. | |
| 2018/0055962 | A1 | 3/2018 | Drmanovic | |
| 2018/0064604 | A1 | 3/2018 | Drmanovic | |
| 2018/0071508 | A1 | 3/2018 | Drmanovic | |
| 2018/0085568 | A1 | 3/2018 | Drmanovic | |
| 2018/0200500 | A1 | 7/2018 | Ziebol et al. | |
| 2018/0214242 | A1 | 8/2018 | Davis et al. | |
| 2018/0214684 | A1 | 8/2018 | Avula et al. | |
| 2018/0250194 | A1 | 9/2018 | Drmanovic | |
| 2018/0256804 | A1 | 9/2018 | Burbank et al. | |
| 2018/0256880 | A1 * | 9/2018 | Follman ................ | A61M 39/20 |
| 2018/0256881 | A1 | 9/2018 | Hitchcock et al. | |
| 2018/0256883 | A1 | 9/2018 | Follman et al. | |
| 2018/0369562 | A1 | 12/2018 | Gardner et al. | |
| 2019/0038888 | A1 | 2/2019 | Gardner | |
| 2019/0099593 | A1 | 4/2019 | Avula et al. | |
| 2019/0117332 | A1 | 4/2019 | Davis et al. | |
| 2019/0201681 | A1 | 7/2019 | Ziebol et al. | |
| 2019/0262525 | A1 | 8/2019 | Wyeth et al. | |
| 2019/0282795 | A1 | 9/2019 | Fangrow | |
| 2019/0351212 | A1 | 11/2019 | Dudar et al. | |
| 2020/0121858 | A1 | 4/2020 | Anderson et al. | |
| 2020/0139037 | A1 | 5/2020 | Ziebol et al. | |
| 2020/0155794 | A1 | 5/2020 | Ziebol | |
| 2020/0197686 | A1 | 6/2020 | Anderson et al. | |
| 2020/0238070 | A1 | 7/2020 | Ryan | |
| 2021/0001110 | A1 | 1/2021 | Bedoe et al. | |
| 2021/0093791 | A1 | 4/2021 | Anderson et al. | |
| 2021/0275707 | A1 | 9/2021 | Jiang et al. | |
| 2021/0322749 | A1 | 10/2021 | Rothenberg et al. | |
| 2021/0322750 | A1 | 10/2021 | Harandi et al. | |
| 2021/0322751 | A1 | 10/2021 | Jiang et al. | |
| 2021/0322752 | A1 | 10/2021 | Jiang et al. | |
| 2022/0152374 | A1 | 5/2022 | Erekovcanski et al. | |
| 2022/0288258 | A1 * | 9/2022 | Gardner ................ | A61M 39/20 |

* cited by examiner

UNIVERSAL DISINFECTING CAP FOR DIFFERENT TYPES OF FEMALE CONNECTORS

BACKGROUND OF THE INVENTION

Field of the Invention

The present disclosure relates generally to caps for medical connectors and, in particular, to a medical cap configured to be attached to different types of female connectors for sealing, cleaning, and disinfecting portions of the different types of female connectors.

Description of Related Art

Vascular access devices (VADs) are commonly used medical devices, which can include intravenous (IV) catheters, such as peripheral catheters or central venous catheters. If not properly maintained or if exposed to a non-sterile environment, the VADs can become contaminated, sealed with blood clots, and/or can spread infection. Further, bacteria and other microorganisms may gain entry into a patient's vascular system from access hubs, ports, or valves upon connection to the VAD to deliver a fluid or pharmaceutical to a patient. Therefore, each access hub (or port/valve or connection) configured for attachment to a VAD is associated with some risk of transmitting a catheter related bloodstream infection (CRBSI) to a patient.

Many medical facilities implement sterile practices and protocols to ensure that VADs and access hubs or ports are used properly and do not become sealed or infected. These protocols often include sterilizing the access hubs, ports, and VADs, as well as flushing the catheter with a flush solution prior to use. Specifically, VAD standards of practice usually recommend flush procedures be performed after catheter placement, before fluid infusion, and before and after drug administration, blood sampling, transfusions, and/or administration of parenteral nutrition. Standards of practice can also require that access hubs, ports, and valves be capped with disinfection caps, when not in use, to prevent microbial ingress into the hub, port, or valve and to sterilize areas of the hub, port, or valve that contact the VAD. Disinfection caps are disposable cap devices that contain an amount of cleaning or disinfecting solution for sterilizing portions of the port, hub, and valve.

Access hubs and ports can have a variety of different types of male or female connectors for securing the hub or port to the VAD. Currently, practitioners often carry several types of caps with them so that they can cap the different types of hubs and ports that may be used for a particular patient. For example, female needleless connectors, as well as intravenous (IV) and hemodialysis lines, by different manufacturers may have different connector designs and may require different caps. In fact, there can be significant variability in needless connector dimensions and design, even for connectors that are configured to satisfy ISO standards. In particular, there are many different types of "female disinfecting cap devices" for disinfecting ISO594-2 type of female threaded fluid luer connectors. Practitioners often must carry these different types (e.g., sizes and designs) of disinfecting caps used with different types of female connectors, each of which may satisfy the ISO standards.

Some examples of universal caps that fit different types of connectors are known. For example, U.S. Pat. No. 10,871,246, entitled "Universal connector or cap for male and female threaded fittings," which is incorporated herein by reference in its entirety, discloses a cap including a threaded protrusion that can engage both a male connector and a female connector. However, there is a need for simpler cap designs that can be manufactured inexpensively and efficiently. There is also a need for caps that can be used with many different types of female connectors, which may be used at a medical facility for different medical procedures. The universal caps of the present disclosure are configured to attach to different types of female medical connectors in a secure manner sufficient for preventing microbial ingress. Further, the universal caps of the present disclosure are configured to be easy to manufacture and assemble.

SUMMARY OF THE INVENTION

According to an aspect of the disclosure, a cap configured to engage different types of female connectors includes a housing having a closed bottom, an open top, and a sidewall extending between the top and the bottom with threads on an inner surface of the sidewall. The cap also includes a sleeve disposed in the housing with threads engaged to the threads of the housing configured to rotate relative to the housing, thereby moving the sleeve through the housing, and a gripper disposed at least partially in the sleeve having at least one flexible leg pressed radially inward by the sleeve as the sleeve moves through the housing. The cap also includes an absorbent support disposed in the gripper configured to clean and/or disinfect portions of the female connector.

In accordance with an embodiment of the present invention, a cap configured to engage different types of female connectors includes a housing having a closed bottom, an open top, and a sidewall extending between the top and the bottom comprising threads on an inner surface of the sidewall; a sleeve disposed in the housing comprising threads engaged to the threads of the housing configured to rotate relative to the housing, thereby moving the sleeve through the housing; a gripper disposed at least partially in the sleeve comprising at least one flexible leg pressed radially inward by the sleeve as the sleeve moves through the housing; and an absorbent support disposed in the gripper configured to clean and/or disinfect portions of the female connector.

In accordance with another embodiment of the present invention, the cap is sized to receive female connectors having different thread configurations and dimensions.

In accordance with another embodiment of the present invention, the cap is sized to receive female connectors having threads with a width at a crest of from about 0.3 mm to about 1.0 mm and a width at a root of the crest from about 0.5 mm to 1.2 mm.

In accordance with another embodiment of the present invention, the female connector comprises a female luer connector comprising a threaded outer surface.

In accordance with another embodiment of the present invention, when the female luer connector is inserted into the housing, the threaded outer surface of the female luer connector contacts the at least one leg of the gripper.

In accordance with another embodiment of the present invention, the absorbent support is configured to clean and/or disinfect at least the threaded outer surface of the female luer connector.

In accordance with another embodiment of the present invention, the housing, sleeve, and gripper comprise a rigid thermoplastic polymer comprising at least one of polyester, polycarbonate, polypropylene, polyethylene, polyethylene terephthalate, or acrylonitrile butadiene styrene.

In accordance with another embodiment of the present invention, the sleeve comprises an inwardly extending protrusion on an inner surface of the sleeve positioned to contact an outer surface of the gripper.

In accordance with another embodiment of the present invention, an inner surface of the sleeve is tapered, such that an inner diameter of the sleeve increases from a top of the sleeve to a bottom of the sleeve.

In accordance with another embodiment of the present invention, the sleeve further includes at least one axially extending tab extending axially from a top of the sleeve beyond the open top of the housing.

In accordance with another embodiment of the present invention, the gripper includes an annular base and the at least one leg extending axially from the annular base.

In accordance with another embodiment of the present invention, the at least one leg includes an inner surface and an outer surface, and wherein at least a portion of the outer surface is sloped towards the annular base of the gripper.

In accordance with another embodiment of the present invention, the gripper includes a plurality of the flexible legs extending from the annular base about a circumference of the annular base.

In accordance with another embodiment of the present invention, the plurality of legs define a substantially cylindrical space that receives the absorbent support.

In accordance with another embodiment of the present invention, the at least one leg includes an inwardly extending protrusion for pressing against the female connector, thereby securing the cap to the female connector.

In accordance with another embodiment of the present invention, rotation of the housing about the sleeve draws the sleeve into the housing causing the sleeve to contact the gripper moving the gripper radially inward.

In accordance with another embodiment of the present invention, a seal is disposed in the housing over the gripper positioned to clean and disinfect the female connector as the female connector is inserted into the housing.

In accordance with another embodiment of the present invention, the seal includes an annular seal having a non-porous foam, such as a closed cell foam.

In accordance with another embodiment of the present invention, the absorbent support includes a sponge.

In accordance with another embodiment of the present invention, the absorbent support includes an open cell foam, such as a porous foam having a thermoplastic elastomer.

In accordance with another embodiment of the present invention, a cleaning solution is absorbed by the absorbent support.

In accordance with another embodiment of the present invention, the cleaning solution includes Isopropyl Alcohol (IPA).

In accordance with another embodiment of the present invention, the cleaning solution includes from about 0.5% to about 3.5% chlorhexidine gluconate and about 70% IPA In accordance with another embodiment of the present invention, a protective cover is provided over the open top of the housing.

In accordance with another embodiment of the present invention, the protective cover is attached to the housing by heat sealing.

DESCRIPTION OF THE INVENTION

Figure 1B:
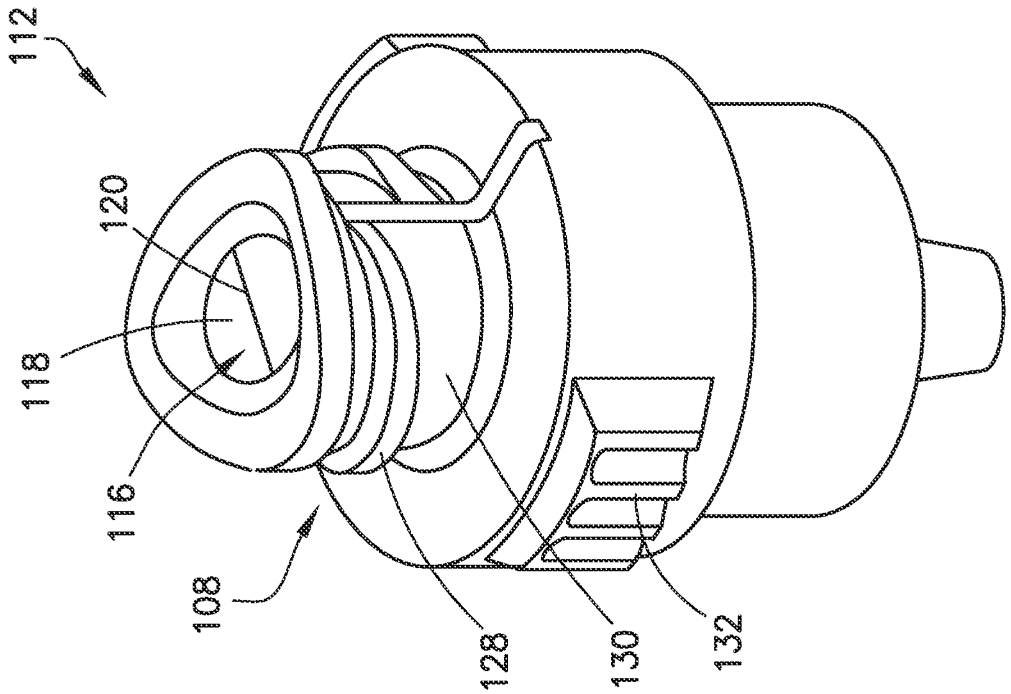
FIG.1B PRIOR ART
FIG. 1B is an example of a female connector including a septum with a slit, as is known in the prior art.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms “upper”, “lower”, “right”, “left”, “vertical”, “horizontal”, “top”, “bottom”, “lateral”, “longitudinal”, and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

The present disclosure is directed to a cap 10 configured to be connected to different types of female medical connectors 112, such as female connectors 112 of an access hub, port, or valve for a VAD, to prevent the connector, port, or VAD from being contaminated by, for example, microbes, debris, or other contaminants. In some cases, the cap 10 can be configured to clean or disinfect the connector 112 or port, ensuring that the connector 112 or port remains sterile prior to use. The cap 10 can be configured to remain in place on a connector 112 or port for at least seven days, which is a maximum time of recommended use permitted by many medical facility sterile practice guidelines. The cap 10 can be configured to engage or be connected to different sizes, configurations, or types of female medical connectors 112. For example, the cap 10 can be configured to engage or be connected to connectors 112 of different designs, configurations, and sizes. In particular, the cap 10 can be configured for use with female connectors 112 having different arrangements of threads, such as threads with different inner or outer diameters or threads with different thread widths (e.g., threads having different widths at the crest and/or root of the thread).

Figure 1A:
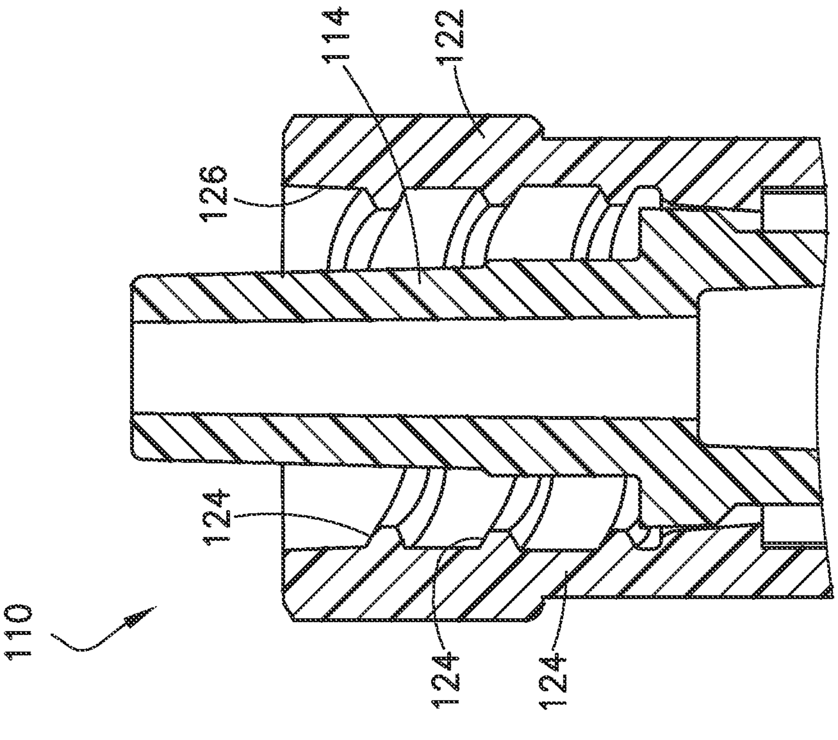
FIG.1A PRIOR ART
FIG. 1A is a cross-sectional view of an exemplary male connector, as is known in the prior art.

As used herein, a "female connector" refers to a connector 112 comprising an opening or port 116 that is configured to receive an elongated member or tubular member of another object or device in order to connect the object or device to the female connector 112. The female connector 112 can comprise an elongated tubular distal portion 108 with a cover or septum 118 over the opening 116. An exemplary female connector 112 including a septum 118 with a slit 120 is shown in FIG. 1B. The female connector 112 can be configured to be connected to or engage various types of male connectors 110. As used herein, a "male connector" refers to a connector 110 comprising an elongated member, such as a tubular member or stem 114, configured to be inserted in a tube or opening having an inner diameter that is larger than an outermost diameter of the male connector 110. An exemplary male connector 110 is shown in FIG. 1A.

In some examples, the cap 10 of the present disclosure is configured to engage a female luer connector 112 having an outer diameter of about 7.0 mm to about 8.0 mm. As used herein, a "luer connector" refers to a connector that includes a tapered portion (i.e., a luer taper) for creating a friction engagement between a tapered stem 114 or elongated member of a male luer connector 110 and a tapered cavity. Specifically, the male luer connector 110 includes a tapered stem 114 or elongated member having a tapered outer surface. The female luer connector 112 can include a tapered cavity configured to receive and engage the tapered stem 114 or elongated member to connect the male luer connector 110 to the female luer connector 112.

In order to secure the male and female connectors 110, 112 together, in some examples, the connectors 110, 112 can include engaging structures, such as threads, for drawing the connectors 110, 112 together. For example, as shown in FIG. 1A, the male luer connector 110 can include an annular shield 122 extending about the tapered stem 114 or elongated member. The annular shield 122 can include threads 124 on an inner surface 126 of the shield 122 configured to engage corresponding threads 128 on an outer surface 130 of the female luer connector 112. For example, as shown in FIG. 1B, the female luer connector 112 includes the threads 128 extending from the outer surface 130 positioned to engage the threads 124 on the inner surface 126 of the annular shield 122 of the male luer connector 110. Twisting the female connector 112 relative to the male connector 110 causes the corresponding threads 124, 128 to engage, which draws the connectors 110, 112 together, such that the tapered stem 114 or elongated member of the male luer connector 110 moves through the opening 116 of the female connector 112. In some examples, the female connector 112 can also include vertical ribs 132 near a proximal end of the female connector 112, which can be used to manipulate the female connector 112 making it easier to twist the female connector 112 relative to another connector or device.

The caps 10 of the present disclosure are configured to engage a variety of different configurations and orientations of female connectors 112, such as different types of female needleless luer connectors. As will be appreciated by those skilled in the art, there are numerous different commercially available medical devices, such as hubs, ports, and valves, which include different variations of female connectors 112. The caps 10 of the present disclosure are configured to adapt or deform so that they can be secured to numerous different types and sizes of connectors 112. For example, the caps 10 of the present disclosure can be configured to attach to female luer connectors 112, such as female Luer-Lok™ connectors by Becton Dickinson and Company. The caps 10 of the present disclosure can also be configured to cover different connector designs including, without limitation, the BD Q-Syte™, BD MaxZero™, BD MaxPlus™, and SmartSite™ needle free connectors by Becton Dickinson and Company. The caps 10 can also be configured to be connected to female connectors by other manufactures including, without limitation, MicroClave® connectors (ICU Medical Inc.) and Ultrasite® connectors (B. Braun Medical Inc.). In other examples, the caps 10 can be configured to be connect to one or more of the following commercially available male connectors: Kendall 2001NP; BD MP5303-C; ICU Med 12664-28; RyMed RYM-5307HPU; B. Braun 470108; Baxter 2C8537; Kawasumi IV-0094; Zyno B2-70071-D; B. Braun 470124; Baxter 2C7462; and Smith's Medical 536035.

FIGS. 2A-8D illustrate an exemplary cap 10 configured to engage and/or to be connected to different types of female connectors 112. In particular, the cap 10 is configured to be used with female connectors 112 with different dimensions and/or different arrangements of threads 128 on the outer surface of the distal end portion 108 of the female connector 112. Previously, different caps may be needed for female connectors with different thread arrangements, meaning that medical practitioners often needed to carry many different types of caps to accommodate different sizes and types of connectors. In some examples, the cap 10 of the present disclosure is configured to cover and seal the distal end portion 108 of the female connector 112 to prevent microbial ingress into the connectors 112. In addition, the caps 10 can include components, such as sponges, abrasive surfaces, and/or cleaning or disinfecting solutions, for cleaning, scrubbing, and disinfecting portions of the connectors 112.

As shown in FIGS. 2A-2D, the cap 10 comprises a housing 12 comprising a closed bottom 14, an open top 16, and a sidewall 18 extending between the bottom 14 and the top 16. The housing 12 can be generally a cup-shaped container sized to engage, cover, and seal ends of different types of female connectors 112. In some examples, the housing 12, along with other components of the cap 10, can be disposable, often formed from thin sheets or layers of an inexpensive material, such as a hard plastic, which can be disposed of after a single use. In some examples, the housing 12 can include axial ridges 20 or similar supporting structures for increasing rigidity or structural integrity of the housing 12. The ridges 20 may also be configured to make the housing 12 easier for the practitioner to grip when rotating the housing 12 in order to connect or disconnect the female connector 112 from the housing 12.

Figure 2A:
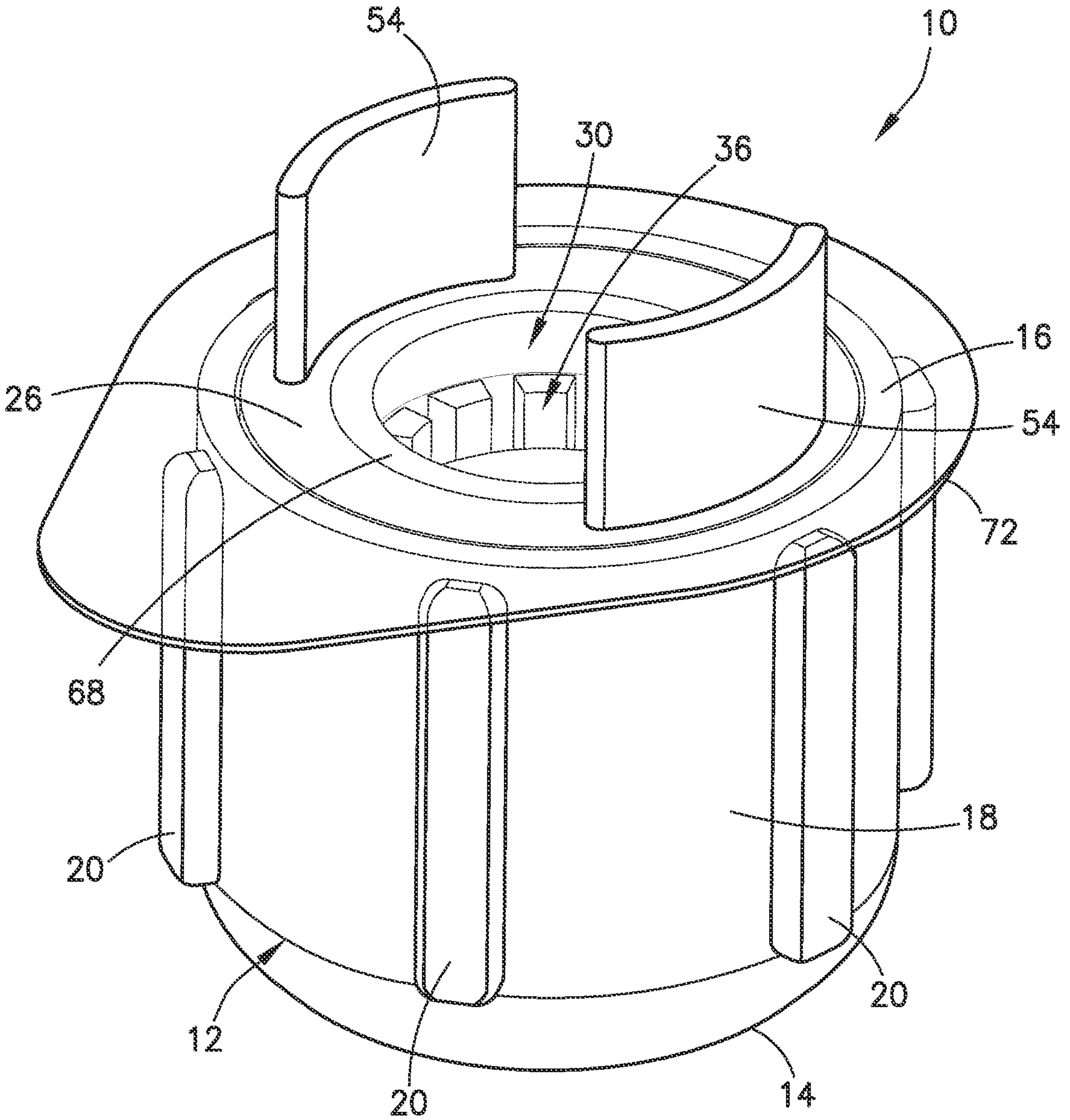
FIG. 2A is a perspective view of a cap for different types of female connectors with a transparent protective cover, according to an aspect of the present disclosure.
Figure 2B:
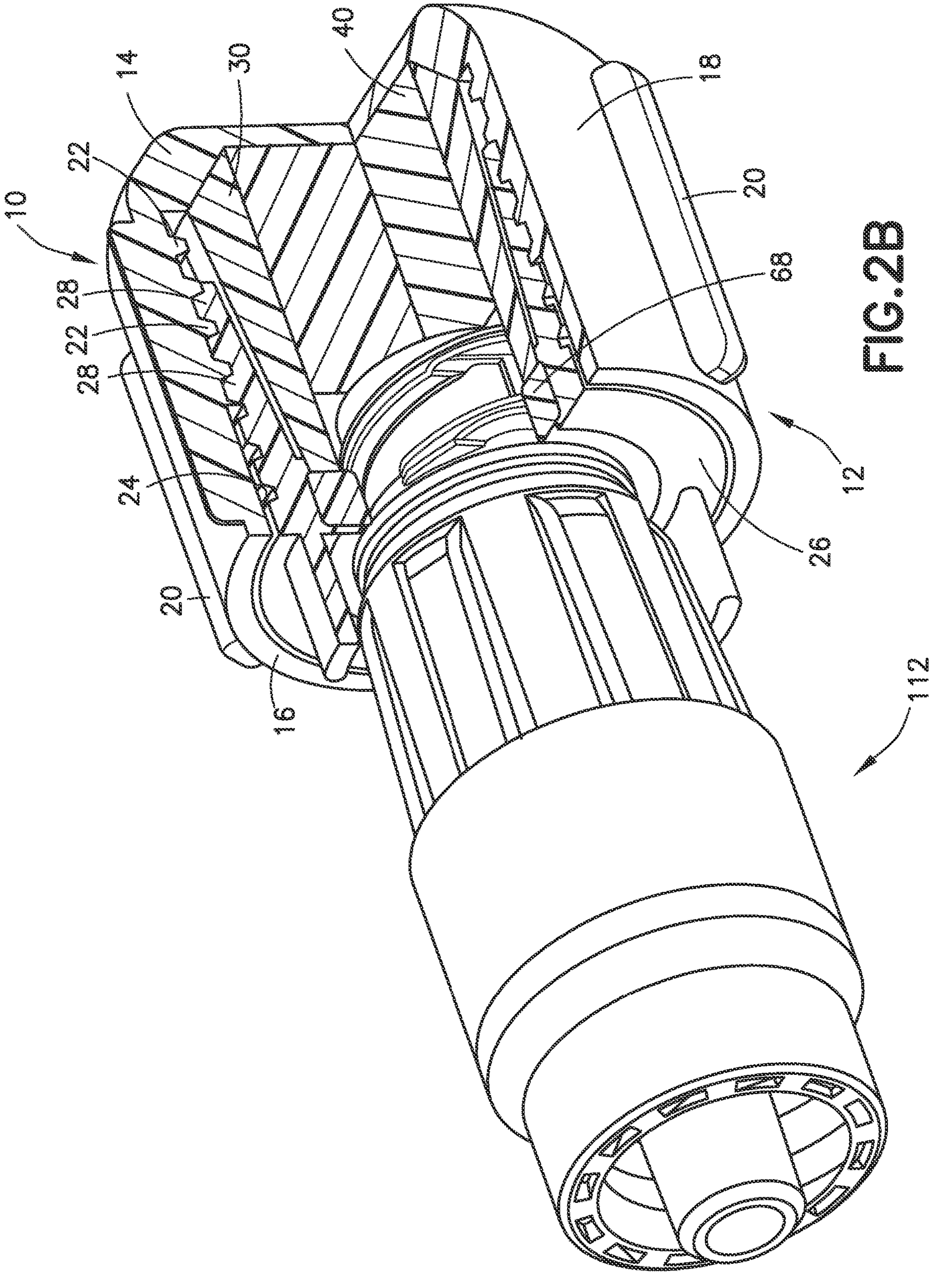
FIG. 2B is a perspective view showing the cap of FIG. 2A connected to a female connector, according to an aspect of the present disclosure.
Figure 2C:
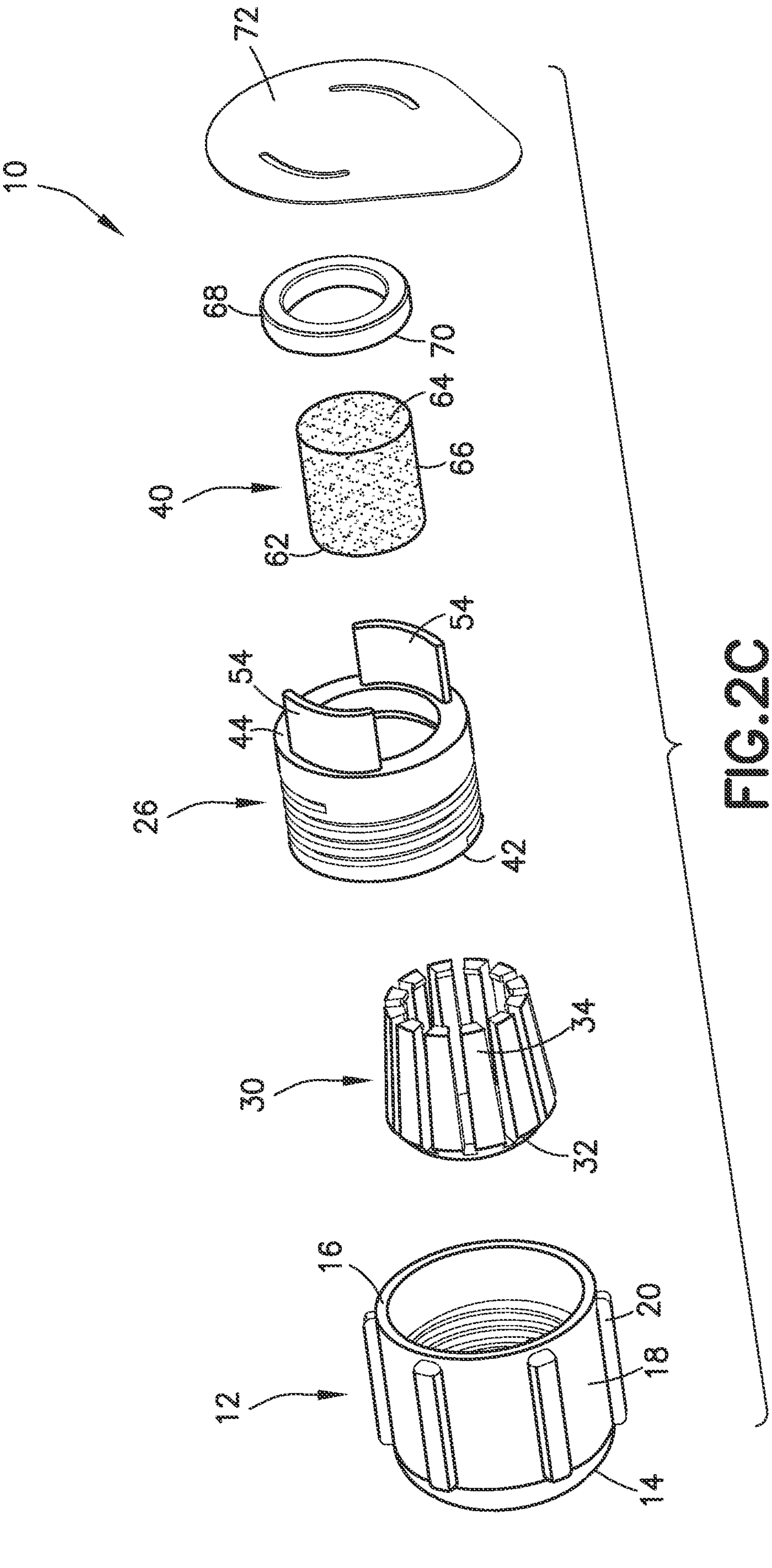
FIG. 2C is an exploded perspective view of the cap of FIG. 2A.
Figure 2D:
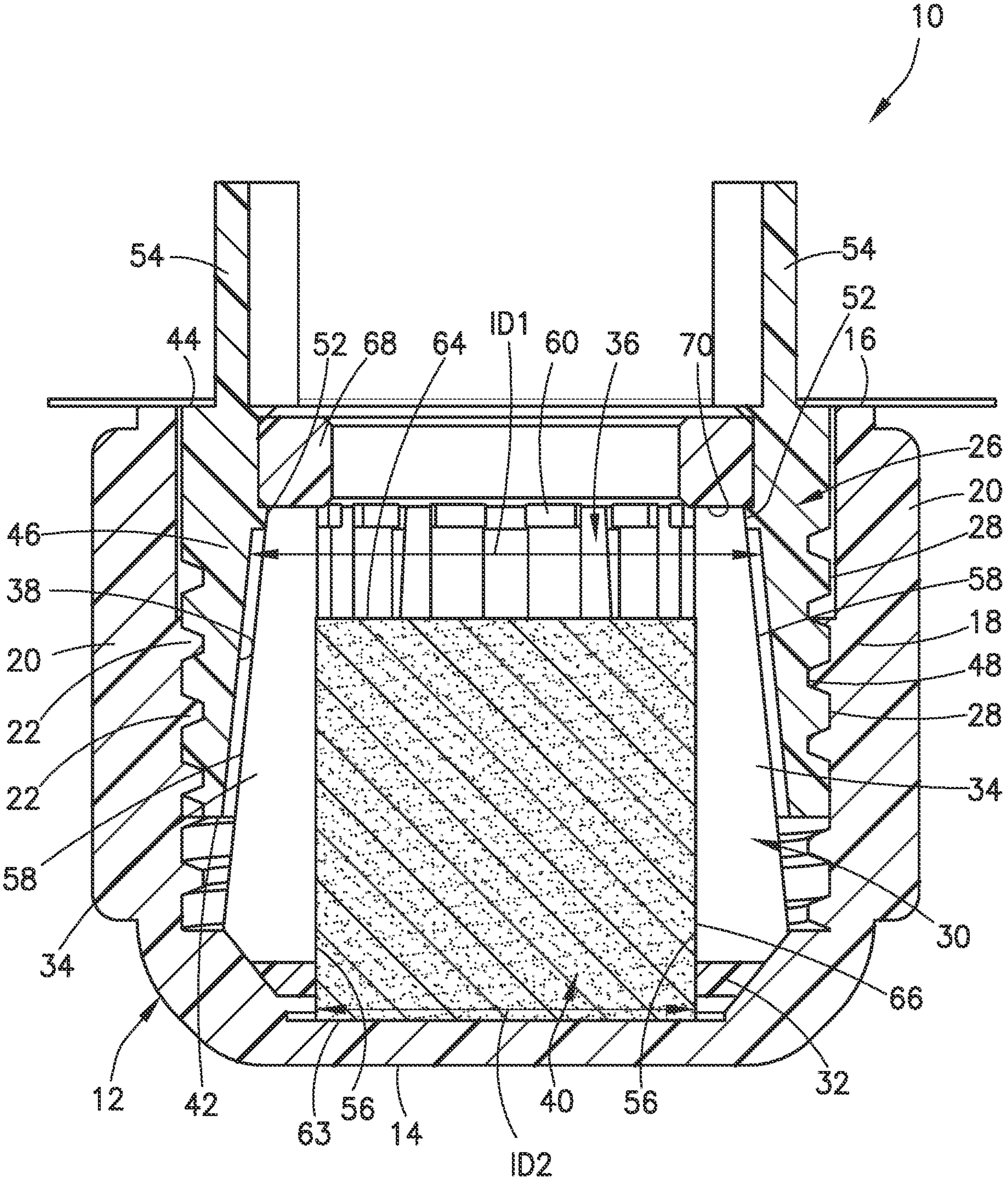
FIG. 2D is a cross-sectional view of the cap of FIG. 2A.
Figure 2E:
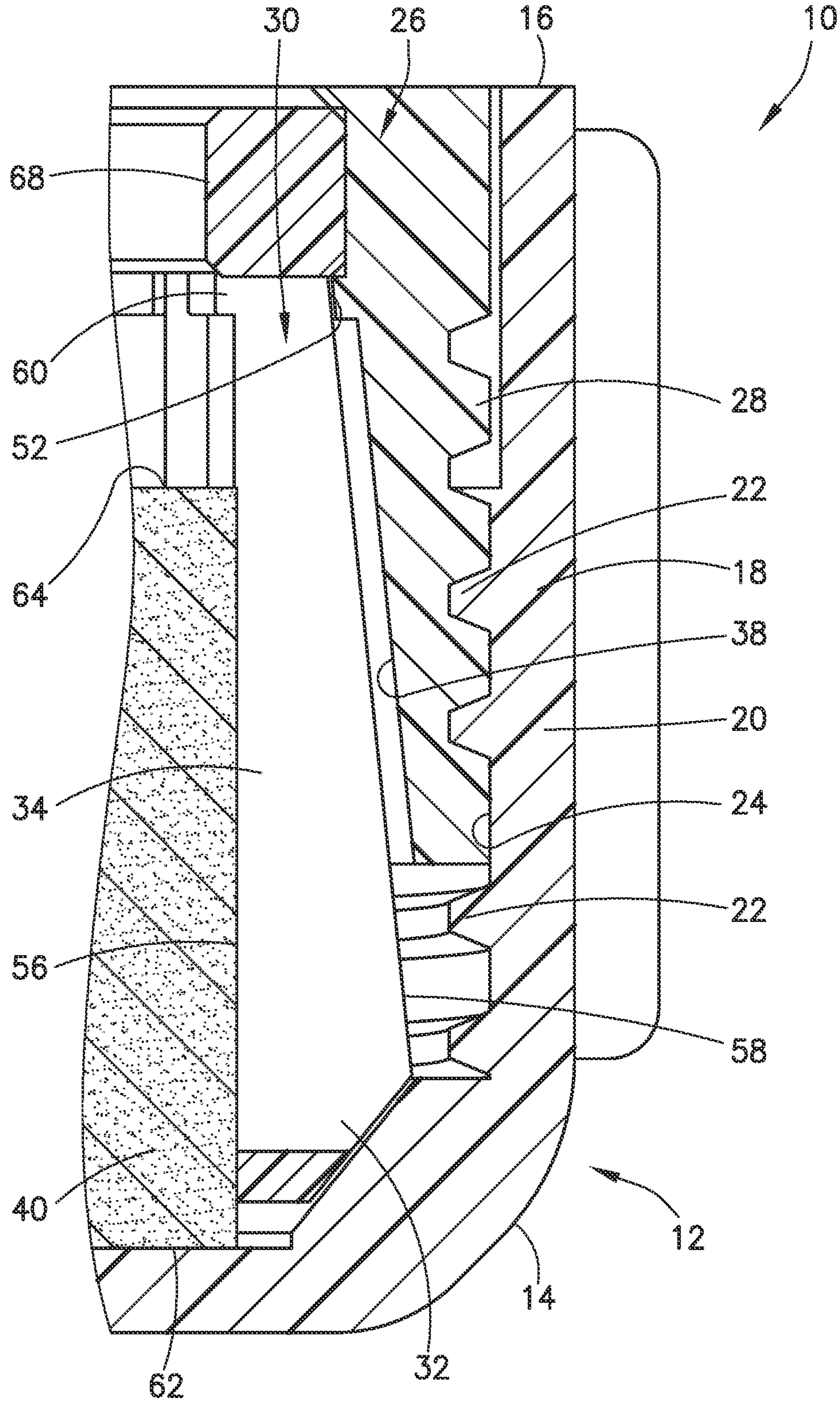
FIG. 2E is an enlarged portion of the cross-sectional view of FIG. 2D showing the cap of FIG. 2A.
Figure 3A:
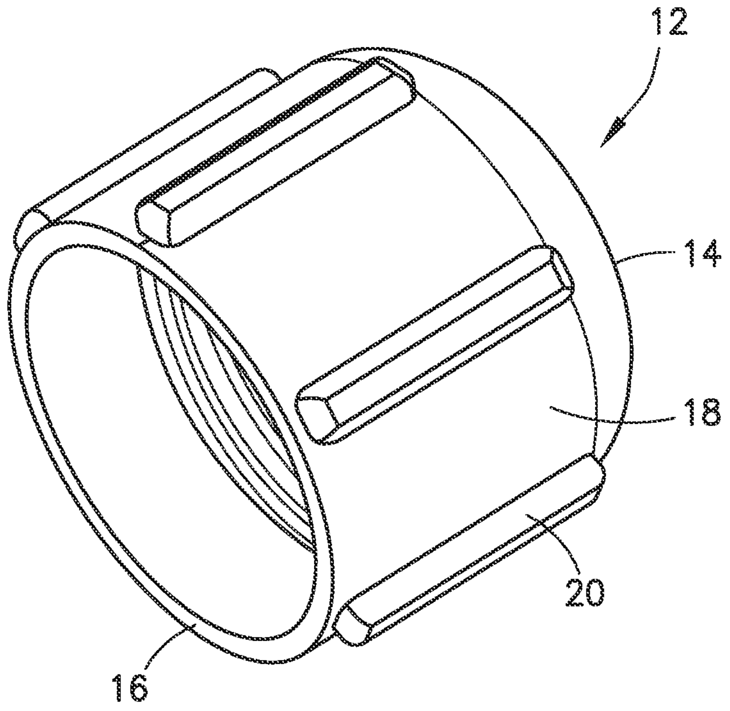
FIG. 3A is a perspective view of a housing of the cap of FIG. 2A, according to an aspect of the present disclosure.
Figure 3B:
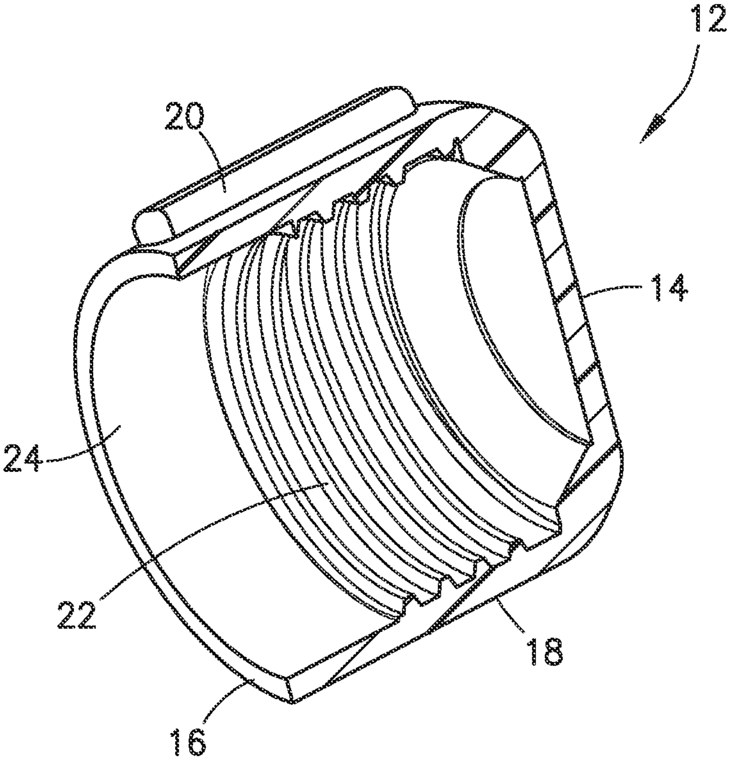
FIG. 3B is a cross-sectional view of the housing of FIG. 3A.
Figure 5B:
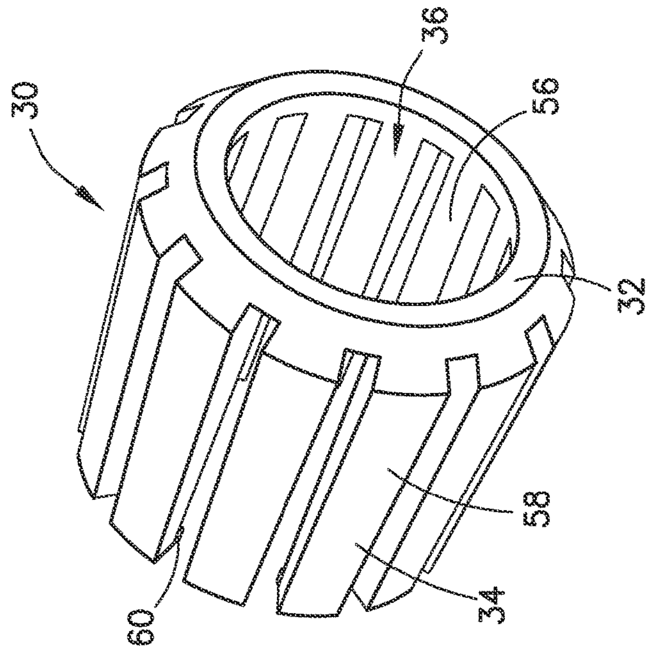
FIG. 5B is a perspective view of a bottom portion of the gripper of FIG. 5A, according to an aspect of the present disclosure.
Figure 5A:
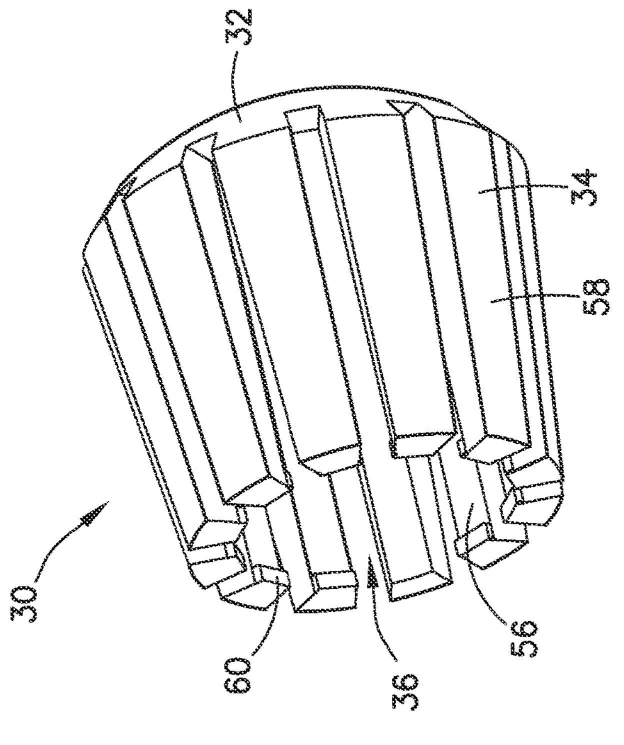
FIG. 5A is a perspective view of a side portion of a gripper of the cap of FIG. 2A, according to an aspect of the present disclosure.
Figure 6:
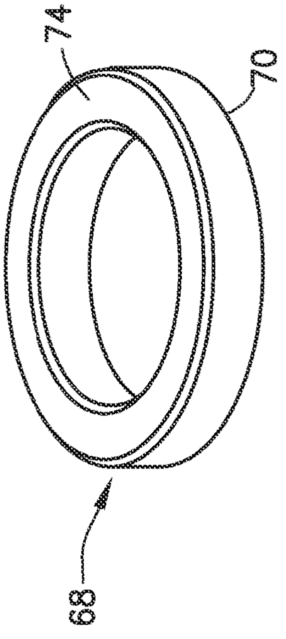
FIG. 6 is a perspective view of an annular seal of the cap of FIG. 2A, according to an aspect of the present disclosure.
Figure 7A:
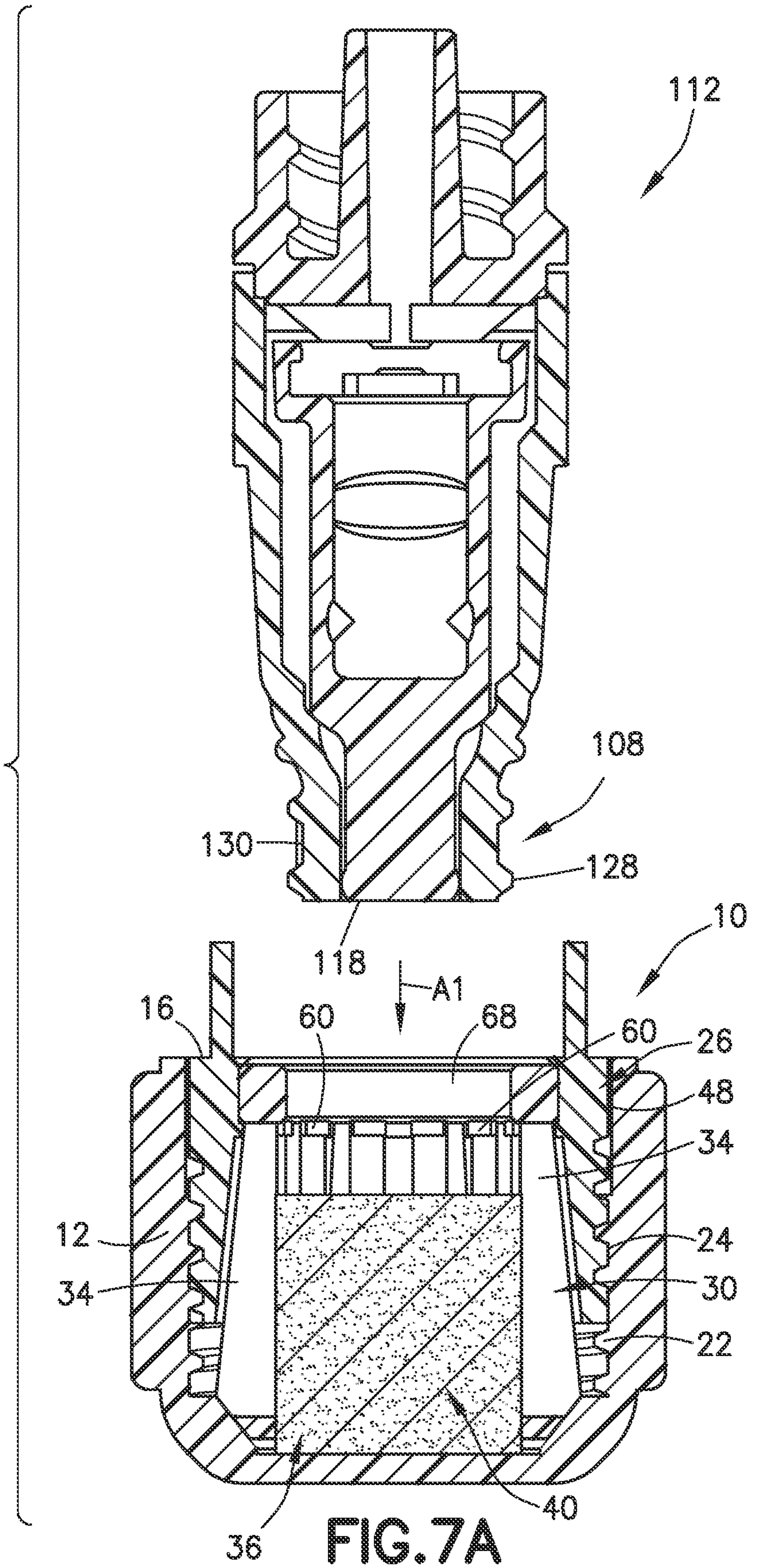
FIG. 7A is a cross-sectional view of a female connector and the cap of FIG. 2A prior to inserting the cap onto the female connector, according to an aspect of the present disclosure.
Figure 7B:
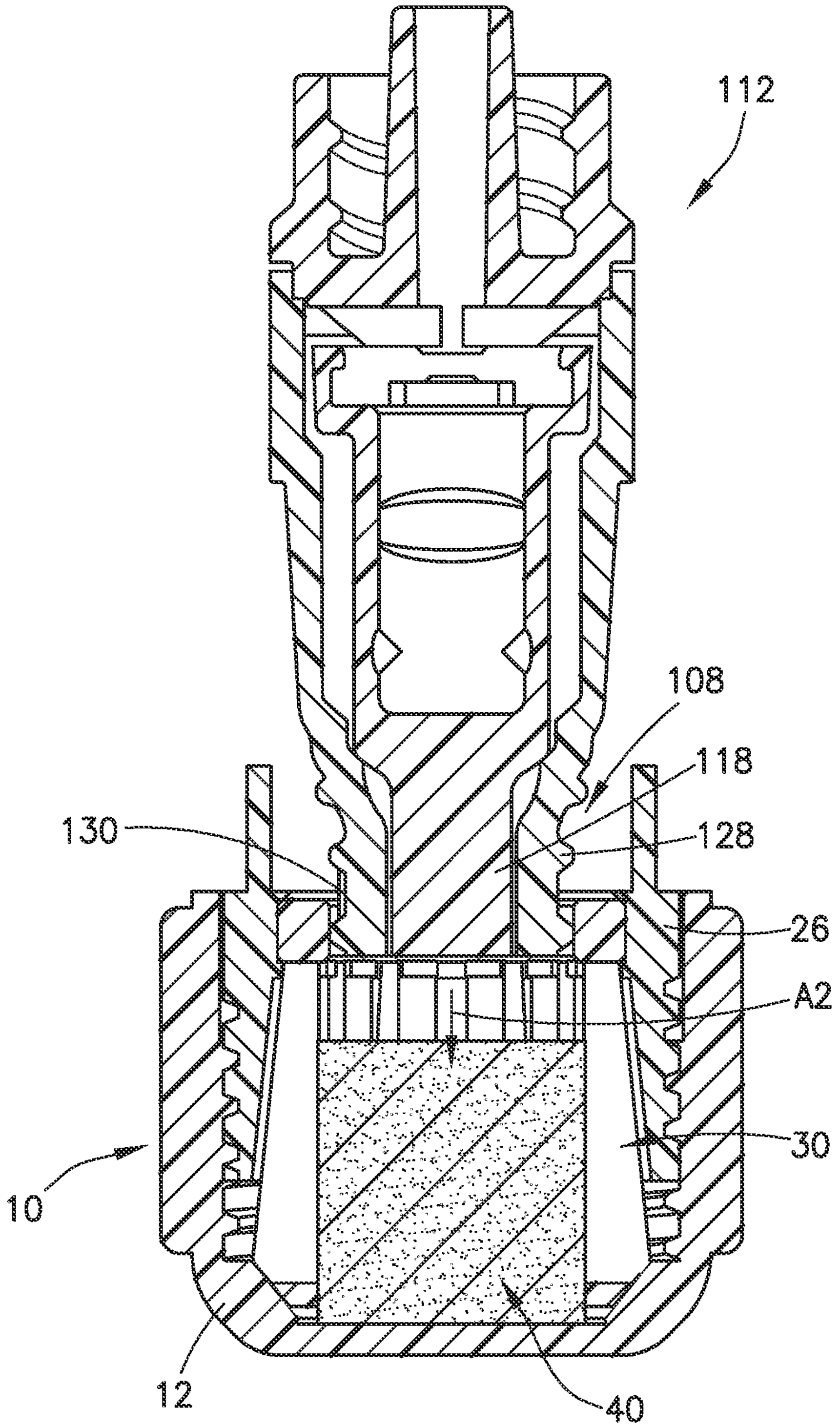
FIG. 7B is a cross-sectional view showing the female connector partially inserted into the cap of FIG. 2A, according to an aspect of the present disclosure.
Figure 7C:
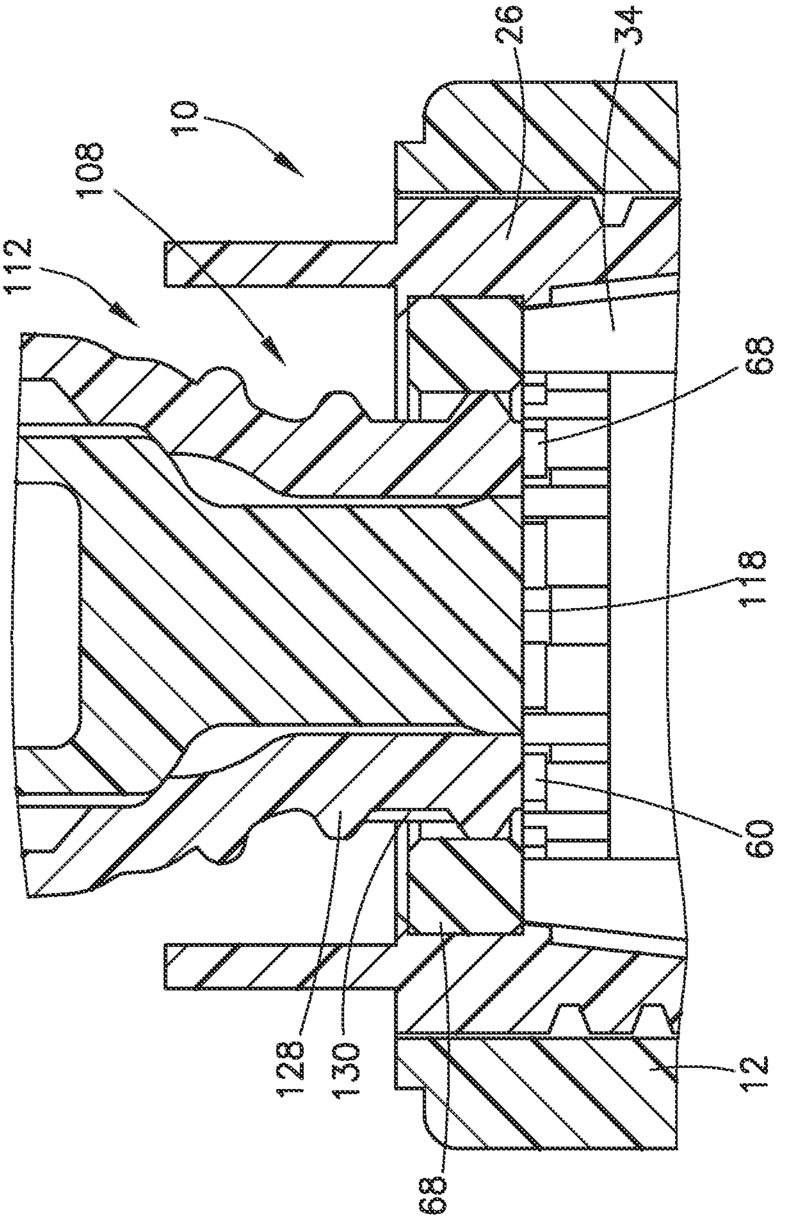
FIG. 7C is an enlarged view of a portion of the cross-sectional view of FIG. 7B.

The housing 12 also includes threads 22 on an inner surface 24 of the housing 12 configured to engage a locking arrangement for securing the cap 10 to the female connector 112. The locking arrangement is adaptable, meaning that it can be used with different types and sizes of female connectors 112. As shown in FIGS. 2C-2E, the locking arrangement includes a sleeve 26 disposed in the housing 12. The sleeve 26 includes threads 28 engaged to the threads 22 of the housing 12 positioned such that rotation of the sleeve 26 relative to the housing 12 moves the sleeve 26 through the housing 12. The locking arrangement also includes a gripper 30 disposed at least partially in the sleeve 26. The gripper 30 includes an annular base 32 positioned proximate to the bottom 14 of the housing 12 and multiple flexible legs 34 extending axially from the base 32 through the housing 12. The legs 34 can be arranged about a circumference of the annular base 32, as shown in FIGS. 5A and 5B, creating a substantially cylindrical space 36 defined by the legs 34. The legs 34 are contacted by an inner surface 38 of the sleeve 26, such that the legs 34 are pressed radially inward by the sleeve 26 as the sleeve 26 moves through the housing 12. The cap 10 also includes an absorbent support 40 disposed in the cylindrical space 36 defined by the legs 34 of the gripper 30. As described in further detail hereinafter, the absorbent support 40 is configured to contact and clean, disinfect, and/or sterilize portions of the female connector 112.

As previously described, the cap 10 of the present disclosure is configured to engage and cover different types and sizes of female connectors 112. In some examples, the cap 10 can be configured to be used with female connectors 112 for the full range of dimensions permitted by various design protocols, such as ISO 80369-7:2016 or ISO 80369-7:2021 (Female Luer Lock Connector dimensions). For example, the cap 10 can be sized to receive female connectors 112 having threads with a width at a crest of each thread of from about 0.3 mm to about 1.0 mm and a width at a root of the thread from about 0.5 mm to about 1.2 mm.

In some examples, components of the cap 10, including the housing 12, gripper 30, and sleeve 26, can be molded parts formed by injection molding or other molding processes known in the art. The separately molded parts can be assembled together during manufacturing to provide a pre-packaged cap 10. Desirably, the pre-packaged cap 10 includes all components needed for sealing, cleaning, and sterilizing the female connector 112. In some examples, the housing 12, sleeve 26, and gripper 30 can be formed from a thermoplastic polymer material, such as polyester, polycarbonate, polypropylene, polyethylene, polyethylene terephthalate, or acrylonitrile butadiene styrene. In some examples, the housing 12 can be formed from a durable material, such as a material having a shore hardness "D" value of less than or equal to about 95. Alternatively, the housing 12 can be formed from a more flexible material, such as a material having a shore hardness "A" value less than or equal to about 95. The sleeve 26 and gripper 30 can be formed from a same material as the housing 12, or may be formed from more rigid materials to withstand forces exerted on the sleeve 26 and gripper 30 as the female connector 112 is inserted into the cap 10.

Figure 4A:
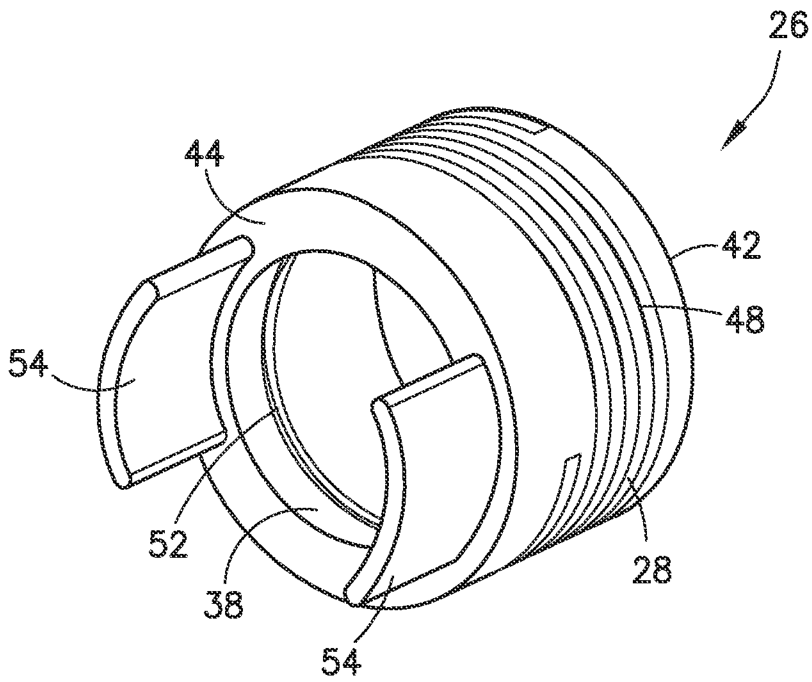
FIG. 4A is a perspective view of a top portion of a sleeve of the cap of FIG. 2A, according to an aspect of the present disclosure.
Figure 4B:
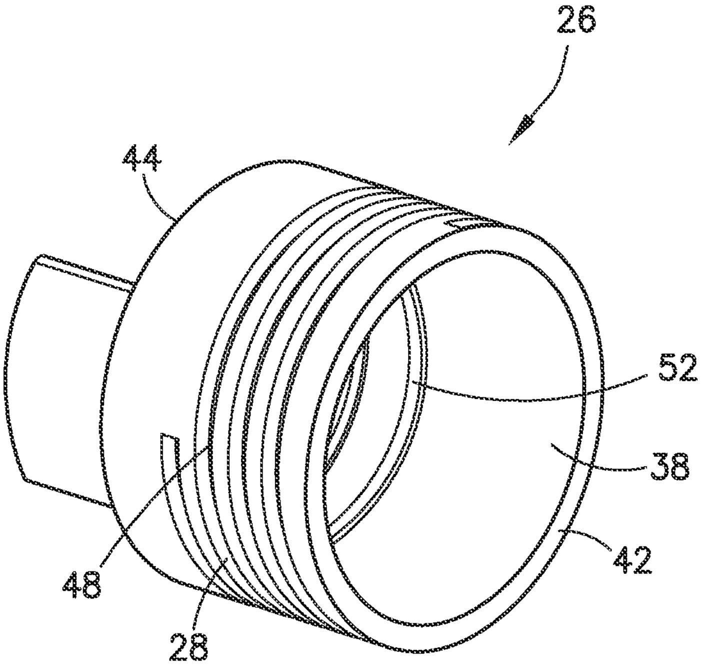
FIG. 4B is a perspective view of a bottom portion of the sleeve of FIG. 4A.

With reference to FIGS. 4A and 4B, the sleeve 26 can be a tubular structure including an open bottom 42, open top 44, and a sidewall 46 extending between the top 44 and the bottom 42. As previously described, an outer surface 48 of the sidewall 46 includes the threads 28 configured to engage the threads 22 on the inner surface 24 of the housing 12 (shown in FIG. 3B). An inner surface 38 of the sidewall 46 of the sleeve 26 is generally smooth. The sleeve 26 further includes an inwardly extending protrusion 52 extending inwardly from the inner surface 38 of the sleeve 26 positioned to contact an outer surface of the gripper 30. The protrusion 52 can be an annular ridge or rib extending radially inward from the inner surface 38 of the sleeve 26 positioned proximate to the top 44 of the sleeve 26. The protrusion 52 is shown in contact with an outer surface of one of the legs 34 of the gripper 30 in FIGS. 2D and 2E. As shown most clearly in FIGS. 2D and 2E, the inner surface 38 of the sleeve 26 is tapered, such that an inner diameter ID1 (shown in FIG. 2D) of the sleeve 26 near the top 44 of the sleeve 26 is smaller than an inner diameter ID2 (shown in FIG. 2D) near the bottom 42 of the sleeve 26. The sleeve 26 also includes axially extending tabs 54 extending from the top 44 of the sleeve 26. For example, as shown most clearly in FIG. 4A, the tabs 54 can be arcuate members positioned on opposite sides of the top 44 of the sleeve 26. The tabs 54 can be configured to allow a practitioner to grasp the sleeve 26 in order to rotate the sleeve 26 or to hold the sleeve 26 in a stationary position while rotating the housing 12 about the sleeve 26.

With reference to FIGS. 5A and 5B, the gripper 30 is a cup-shaped structure including the annular base 32 and the multiple axially extending legs 34. For example, as shown in FIGS. 5A and 5B, the gripper 30 can include twelve legs 34 equidistantly spaced about the circumference of the annular base 32. In other examples, the gripper 30 can include fewer or more than twelve legs 34 depending, for example, on dimensions of the gripper 30 and other components of the cap 10. As previously described, the legs 34 positioned about the circumference of the annular base 32 define the cylindrical cavity space 36 or interior of the gripper 30. Each leg 34 includes an inner surface 56 and an outer surface 58. Portions of the outer surface 58 are sloped or angled towards the base 32 of the gripper 30. For example, the outer surfaces 58 of the legs 34 can be sloped or angled to match the taper of the inner surface 38 of the sleeve 26. The inner surfaces 56 of the legs 34 are generally straight or vertical, meaning that the inner surfaces 56 of the legs 34 define the cylindrical space 36 sized to receive the cylindrical absorbent support 40. In some examples, the legs 34 also include an inwardly directed protrusion or lip 60 on a top or free end of each leg 34. The protrusions or lips 60 are positioned to press against the distal end portion 108 of the female connector 112 for securing the female connector 112 to the cap 10.

With reference again to FIGS. 2C-2E, the absorbent member or support structure (referred to herein as the absorbent support 40) is provided for cleaning and disinfecting portions of the female connectors 112. In particular, absorbent support 40 can be configured to clean and disinfect surfaces of the distal end portion 108, opening or port 116, and septum 118 of the female connector 112. As shown in FIGS. 2C-2E, the absorbent support 40 is a cylindrical structure including a bottom surface 62 proximate to the bottom 14 of the housing 12, a top surface 64, and a cylindrical side 66 extending therebetween. The absorbent support 40 can be formed from an absorbent material capable of absorbing a cleaning or disinfecting solution for cleaning and/or disinfecting portions of the female connector 112. The material of the absorbent support 40 can be abrasive with sufficient texture, friction, and/or anti-slip properties to scrub surfaces of the connector 112 to mechanically remove microbes, debris, and other contaminants from surfaces of the connector 112. For example, the absorbent support 40 can comprise a thermoplastic elastomer, such as polypropylene, polyethylene, or synthetic or natural rubber (e.g., isoprene).

In some examples, the absorbent support 40 can comprise a porous foam (e.g., an open cell foam) or sponge capable of absorbing the cleaning or disinfecting solution. For example, the foam material can be a Plastazote® foam, which is an engineered polymer foam by Zotefoams PCL. In other examples, the foam material can be a polyurethane foam, as known in the art, including an open cell structure capable of absorbing a disinfectant or cleaning solution.

Desirably, a porosity of the absorbent support 40 should be optimized so that the material is abrasive enough to scrub or mechanically remove objects from surfaces of the connector 112, while, at the same time, limiting ingress of cleaning or disinfecting solution into portions of the connectors 112. Further, a height of the absorbent support 40 and/or amount of cleaning or disinfecting solution contained therein can be optimized for use with both short and tall connectors 112. As used herein, a "short connector" refers to a connector that does not insert very far into the cap 10. A "tall connector" refers to a connector that inserts into the cap 10 by a substantial distance, such that a distal end of the connector 112 is proximate to the bottom 14 of the housing 12. In particular, the height of the absorbent support 40 and amount of cleaning or disinfecting solution contained therein should be large enough so that sufficient cleaning solution is released from the absorbent support 40 when the cap 10 is attached to a short connector to disinfect surfaces of the short connector. However, the height of the absorbent support 40 and amount of cleaning solution may be somewhat limited so that liquid ingress into a lumen of the connector 112 does not occur when the cap 10 is attached to a taller connector.

The absorbent support 40 can be provided (i.e., pre-soaked) with the cleaning or disinfecting solution. For example, the cleaning or disinfecting solution can be an antimicrobial, anti-fungal, antibacterial, or antiviral solution that cleans and sterilizes surfaces of the connectors 112. In some examples, the cleaning solution can be isopropyl alcohol (IPA), such as about 70% IPA. In other examples, the cleaning solution can be about 0.5% to about 3.5% chlorhexidine gluconate in combination with about 70% IPA. A chlorohexidine composition may be beneficial because it has a slower evaporation rate than IPA and, therefore, provides a more persistent disinfectant activity after the cap 10 is removed from the connector 112 and before the VAD is connected to the hub, port, or valve.

In some examples, the cap 10 further comprises a seal 68 that covers the absorbent support 40. As shown most clearly in FIG. 6, the seal 68 can be an annular structure including a bottom surface 70 configured to contact top portions of the legs 34 of the gripper 30 and a top surface 74 positioned proximate to the top 16 of the housing 12. Specifically, as shown in FIGS. 2D and 2E, the seal 68 can be positioned in the housing 12 over the gripper 30, such that the female connector 112 passes through the annular seal 68 into the cylindrical space 36 defined by the legs 34 of the gripper 30. The seal 68 is positioned to clean and disinfect the distal end portion 108 of the female connector 112 as the female connector 112 is inserted into the housing 12. The seal 68 can be formed from a non-absorbent and/or non-porous material in order to prevent cleaning solution from leaking from the cap 10 when the female connector 112 is attached thereto. For example, the seal 68 can be formed from a non-porous foam material, such as a closed cell foam, comprising a thermoplastic elastomer.

With continued reference to FIGS. 2A-2E, the cap 10 can further comprise a removable and/or disposable protective cover 72. The protective cover 72 is positioned over the open top 16 of the housing 12. The protective cover 72 is provided to protect components and portions of the cap 10, such as the inner surface 24 of the housing 12, the seal 68, and the absorbent support 40. In particular, the protective cover 72 can protect the cap 10 during transport and storage to prevent contamination and to prevent the cleaning or disinfecting solution from evaporating prior to use. The protective cover 72 can comprise a sheet, such as a polymer film, with adhesive on a first side of the sheet for removably mounting the protective cover 72 to the open top 16 of the housing 12. Alternatively, the protective cover 72 can be removably mounted to the open top 16 of the housing 12 by heat sealing. The protective cover 72 can be formed from a material that is impervious or substantially impervious to air, so that the cleaning or disinfecting solution on the absorbent support 40 does not evaporate or dry-out prior to use of the cap 10. Accordingly, the protective cover 72 can increase a shelf life of the cap 10, as well as prevent microbes and other debris from collecting in the cap 10 prior to use.

In order to connect the cap 10 to a female connector 112, such as the female connector 112 shown in FIGS. 7A-8D, the practitioner first removes any packaging from the cap 10 and removes the protective cover 72 from the open top 16 of the housing 12. Once the protective cover 72 is removed, the practitioner moves the female connector 112 toward the housing 12, as shown by arrow A1 in FIG. 7A, causing the threads 128 of the female connector 112 to move towards the seal 68 positioned proximate to the open top 16 of the housing 12. The practitioner then applies pressure to the female connector 112, causing the distal end portion 108 of the female connector 112 to move through the annular seal 68. For example, threads 128 of the female connector 112 can press against and deform the seal 68, thereby allowing the female connector 112 to move through a central opening of the seal 68 into the housing 12, as shown in FIGS. 7B and 7C. As previously described, the seal 68 can be formed from an abrasive material, meaning that the seal 68 can remove microbes and other debris from surfaces of the female connector 112, as the female connector 112 passes through the seal 68.

Figure 8A:
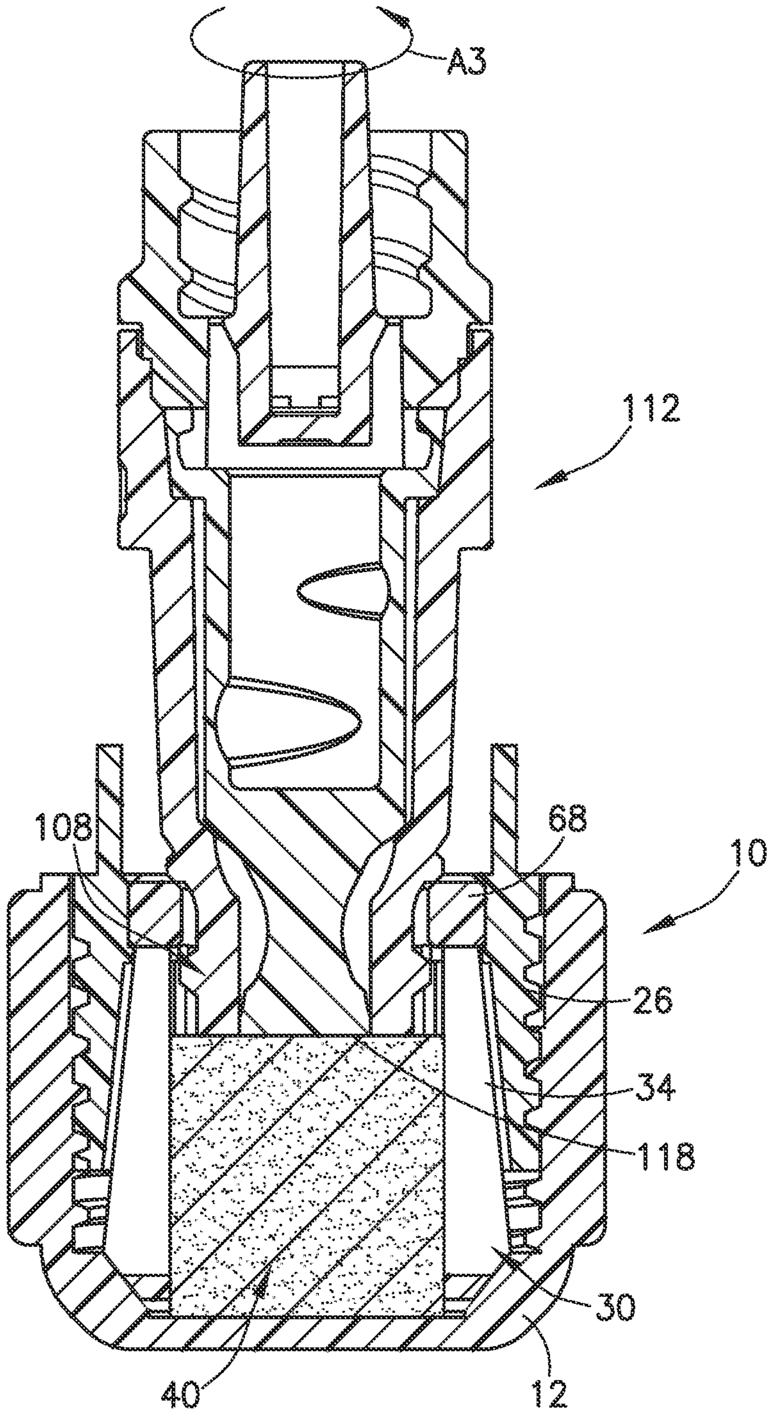
FIG. 8A is a cross-sectional view of a female connector inserted into the cap of FIG. 2A, according to an aspect of the present disclosure.
Figure 8B:
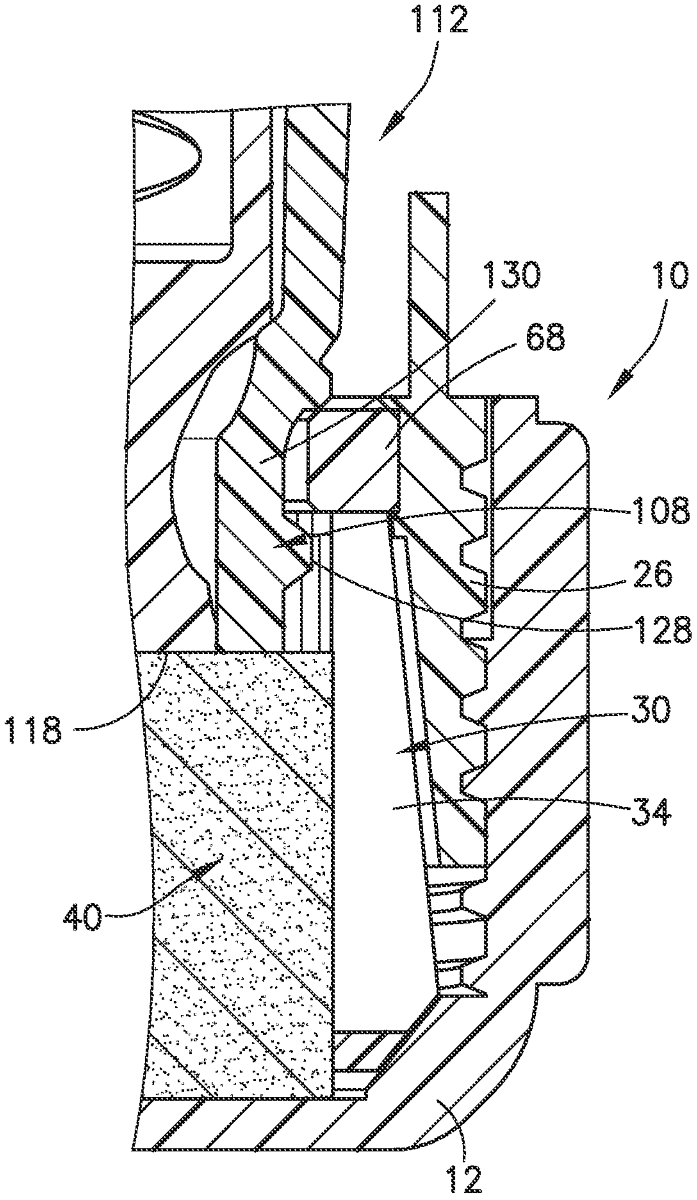
FIG. 8B is an enlarged portion of the cross-sectional view of FIG. 8A.
Figure 8C:
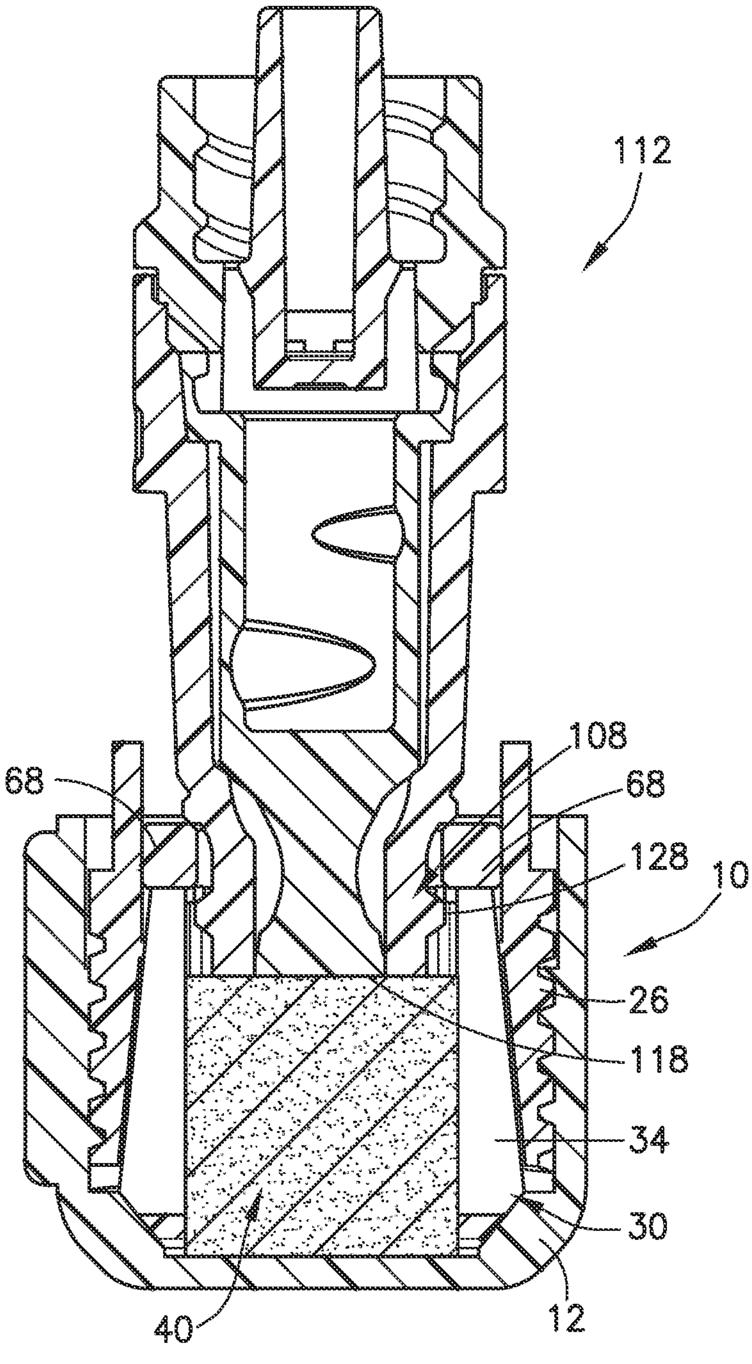
FIG. 8C is a cross-sectional view of a female connector inserted into the cap of FIG. 8A after rotating the cap to move the sleeve through the cap, according to an aspect of the present disclosure.
Figure 8D:
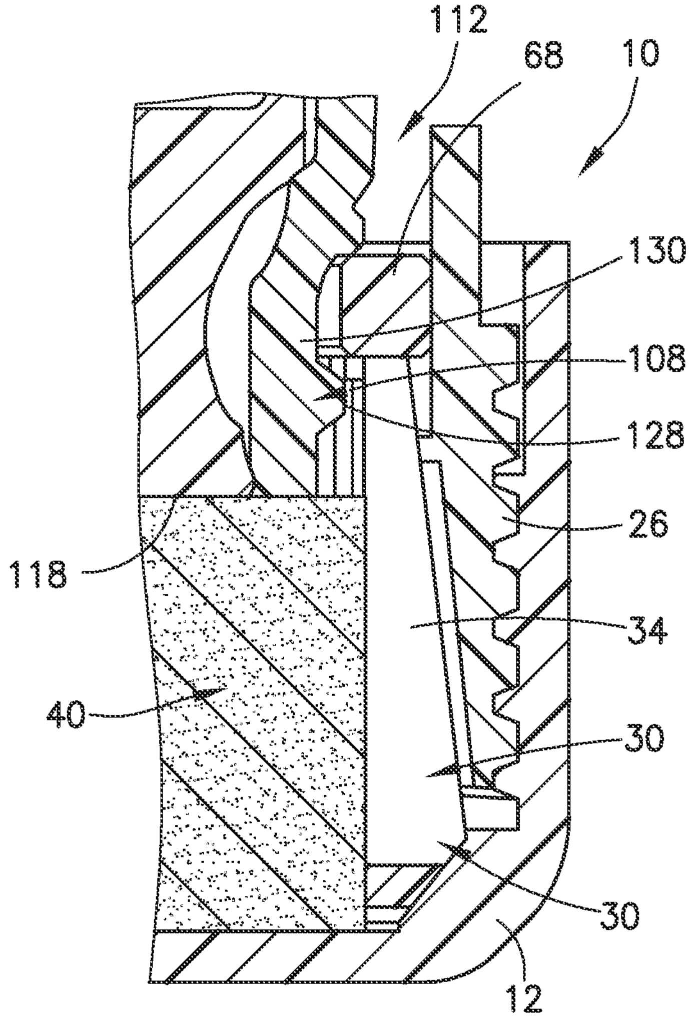
FIG. 8D is an enlarged portion of the cross-sectional view of FIG. 8C.

Continued movement of the female connector 112 in the direction of arrow A1 (shown in FIG. 7A), causes the protrusion or lips 60 at the ends of the legs 34 of the gripper 30 to deflect radially outwardly, allowing the distal end portion 108 and septum 118 of the female connector 112 to move into the cylindrical space 36 defined by the legs 34 of the gripper 30, as shown in FIGS. 8A and 8B. Once threads 128 of the female connector 112 move past the lip 60, the lip 60 can deflect radially inward to retain the distal end portion 108 of the female connector 112 within the cylindrical cavity 36 of the gripper 30.

Once the distal end portion 108 of the female connector 112 is partially in the cylindrical cavity 36 (as shown in FIGS. 8A and 8B), the practitioner can tighten the housing 12 of the cap 10 onto the female connector 112 by rotating the housing 10 relative to the sleeve 26 in a direction of arrow A3 (shown in FIG. 8A) using the tabs 54. Specifically, rotating the housing 12 relative to the sleeve 26 causes the sleeve 26 to move farther into the housing 12 due to the rotational engagement between the threads 28 on the outer surface 48 of the sleeve 26 and threads 22 on the inner surface 24 of the housing 12. Moving the sleeve 26 farther into the housing 12 causes the protrusion 52 on the inner surface 38 of the sleeve 26 to press against the legs 34 of the gripper 30, thereby deflecting the legs 34 radially inward against the distal end portion 108 of the female connector 112. The inward movement of the legs 34 enhances the engagement between the legs 34 and the distal end portion 108 of the female connector 112, thereby securing the cap 10 to the female connector 112. The cap 10 is shown in a fully secured position, with the bottom 42 of the sleeve 26 proximate to the bottom 14 of the housing 12 in FIGS. 8C and 8D.

Drawing the female connector 112 into the housing 12 to the fully secured position (shown in FIGS. 8C and 8D) causes the distal end portion 108 and septum 118 of the female connector 112 to contact a top surface of the absorbent support 40. The contact between the female connector 112 and the absorbent support 40 may compress the absorbent support 40, releasing cleaning or disinfecting solution from the absorbent support 40. The cleaning or disinfecting solution contacts portions of the female connector 112, such as the distal end portion 108, septum 118, and threads 128 of the female connector 112, for cleaning, disinfecting, and sterilizing the female connector 112. As previously described, contact between abrasive surfaces of the absorbent support 40 and surfaces of the female connector 112 may also mechanically remove microbes and other debris from the female connector 112, which contributes to the cleaning effect provided by the cap 10.

In order to remove the cap 10 from the female connector 112, the practitioner first rotates the housing 12 relative to the sleeve 26 in an opposite direction, (e.g., opposite direction from arrow A3 shown in FIG. 8A) by grasping and applying pressure to the tabs 54, causing the sleeve 26 to retract through the housing 12 toward the top 16 of the housing 12 due to the rotational engagement between the threads 28 of the sleeve 26 and the threads 22 of the housing 12. Moving the sleeve 26 towards the top 16 of the housing 12 reduces pressure on the legs 34 of the gripper 30, allowing the legs 34 to move radially outward away from the distal end portion 108 of the female connector 112. The radial outward movement of the legs 34 releases the female connector 112 from the gripper 30. Once the female connector 112 is released from the gripper 30, the practitioner can pull the female connector 112 axially away from the cap 10 with sufficient force to pull the distal end portion 108 of the female connector 112 through the annular seal 68, thereby releasing the female connector 112 from the cap 10. Once the female connector 112 is released from the cap 10, a VAD can be connected to the hub, port, or valve through the female connector 112, as previously described.

While examples of the disinfecting cap 10 and methods of use of the present disclosure are shown in the accompanying figures and described hereinabove in detail, other examples will be apparent to, and readily made by, those skilled in the art without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:

1. A cap configured to engage female connectors, comprising:

a housing comprising a closed bottom, an open top, and a sidewall extending between the top and the bottom comprising threads on an inner surface of the sidewall;

a sleeve disposed in the housing comprising threads engaged to the threads of the housing configured to rotate relative to the housing, thereby moving the sleeve through the housing;

a gripper disposed at least partially in the sleeve comprising at least one flexible leg pressed radially inward by the sleeve as the sleeve moves through the housing, wherein rotation of the housing about the sleeve draws the sleeve into the housing causing the sleeve to contact the gripper moving the gripper radially inward; and an absorbent support disposed in the gripper configured to clean and/or disinfect portions of the female connector.

2. The cap of claim 1, wherein the cap is sized to receive female connectors having different thread configurations and dimensions.

3. The cap of claim 2, wherein the cap is sized to receive female connectors having threads with a width at a crest of from about 0.3 mm to about 1.0 mm and a width at a root of the crest from about 0.5 mm to 1.2 mm.

4. The cap of claim 1, wherein the female connector comprises a female luer connector comprising a threaded outer surface, and wherein, when the female luer connector is inserted into the housing, the threaded outer surface of the female luer connector contacts the at least one leg of the gripper.

5. The cap of claim 4, wherein the absorbent support is configured to clean and/or disinfect at least the threaded outer surface of the female luer connector.

6. The cap of claim 1, wherein the housing, sleeve, and gripper comprise a rigid thermoplastic polymer comprising at least one of polyester, polycarbonate, polypropylene, polyethylene, polyethylene terephthalate, or acrylonitrile butadiene styrene.

7. The cap of claim 1, wherein the sleeve comprises an inwardly extending protrusion on an inner surface of the sleeve positioned to contact an outer surface of the gripper.

8. The cap of claim 1, wherein an inner surface of the sleeve is tapered, such that an inner diameter of the sleeve increases from a top of the sleeve to a bottom of the sleeve.

9. The cap of claim 1, wherein the sleeve further comprises at least one axially extending tab extending axially from a top of the sleeve beyond the open top of the housing.

10. The cap of claim 1, wherein the gripper comprises an annular base and the at least one leg extending axially from the annular base.

11. The cap of claim 10, wherein the at least one leg comprises an inner surface and an outer surface, and wherein at least a portion of the outer surface is sloped towards the annular base of the gripper.

12. The cap of claim 10, wherein the gripper comprises a plurality of the flexible legs extending from the annular base about a circumference of the annular base, and wherein the plurality of legs define a substantially cylindrical space that receives the absorbent support.

13. The cap of claim 1, wherein the at least one leg comprises an inwardly extending protrusion for pressing against the female connector, thereby securing the cap to the female connector.

14. The cap of claim 1, further comprising a seal disposed in the housing over the gripper positioned to clean and disinfect the female connector as the female connector is inserted into the housing, wherein the seal comprises an annular seal comprising a non-porous foam, such as a closed cell foam.

15. The cap of claim 1, wherein the absorbent support comprises a sponge and/or a porous open cell foam comprising a thermoplastic elastomer.

16. The cap of claim 1, further comprising a cleaning solution absorbed by the absorbent support, wherein the cleaning solution comprises Isopropyl Alcohol (IPA).

17. The cap of claim 16, wherein the cleaning solution comprises from about 0.5% to about 3.5% chlorhexidine gluconate and about 70% IPA.

18. The cap of claim 1, further comprising a protective cover over the open top of the housing.

19. The cap of claim 18, wherein the protective cover is attached to the housing by heat sealing.

* * * * *